United States Patent [19]

Miller

[11] 4,001,282

[45] Jan. 4, 1977

[54] PROCESS FOR PRODUCING GAMMA-BUTYROLACTONE

[75] Inventor: Elwood M. Miller, Pittsfield, Mass.

[73] Assignee: General Electric Company, Pittsfield, Mass.

[22] Filed: Feb. 12, 1973

[21] Appl. No.: 331,530

[52] U.S. Cl. .............................................. 260/343.6
[51] Int. Cl.$^2$ ..................................... C07D 307/32
[58] Field of Search ................................ 260/343.6

[56] References Cited

UNITED STATES PATENTS

| | | | |
|---|---|---|---|
| 2,072,861 | 3/1937 | Amend et al. | 260/343.6 |
| 3,065,243 | 11/1962 | Dunlop et al. | 260/343.6 |
| 3,758,512 | 9/1973 | Hanetaka et al. | 260/343.6 |

FOREIGN PATENTS OR APPLICATIONS

| | | | |
|---|---|---|---|
| 1,901,870 | 9/1969 | Germany | 260/343.6 |

Primary Examiner—Henry R. Jiles
Assistant Examiner—C. M. S. Jaisle
Attorney, Agent, or Firm—William F. Mufatti; Granville M. Pine; Edward A. Hedman

[57] ABSTRACT

Gamma-Butyrolactone is produced by passing vaporized maleic acid/anhydride or succinic acid/anhydride or mixtures thereof, water, and hydrogen, over a metallic catalyst capable of hydrogenolyzing a carboxylic group to a methyleneoxy group. Even though water is also a byproduct of the reaction, very high yields of gamma-butyrolactone are obtained, and the added water plays a key role in extending catalyst life by suppressing the formation of coke and tar.

16 Claims, No Drawings

PROCESS FOR PRODUCING GAMMA-BUTYROLACTONE

This invention relates to an improved process for producing gamma-butyrolactone from maleic acid/anhydride and/or succinic acid/anhydride in the vapor phase.

BACKGROUND OF THE INVENTION gamma-Butyrolactone, which is useful, for example, as a dye solvent, as a spinning solvent for synthetic fibers, and as an intermediate in the manufacture of pyrrolidone and 1,4-butanediol, can be made in a number of ways. In the laboratory, for example, tetrahydrofuran can be oxidized with ruthenium tetroxide in carbon tetrachloride at 0° C.; and succinic anhydride can be reduced with sodium amalgam. Commercially attractive processes involve the passage of a vaporized feed of maleic acid/anhydride or succinic acid/anhydride with hydrogen over a metallic catalyst capable of hydrogenolyzing a carboxylic group to a methyleneoxy group. One such process is described in U.S. Pat. No. 3,065,243, in which a feed compound, such as maleic anhydride, succinic anhydride, acids or esters thereof is vaporized and then the vapors are passed with hydrogen over a reduced copper-chromite catalyst. The vaporized feed compounds can be used per se or they can be mixed with an organic solvent such as the lactone, or a lower alcohol, such as methanol, before being fed to the catalyst. It is also known, e.g., from the disclosure in U.K. Pat. No. 1,168,220, that feed compounds of purified maleic acid/anhydride or succinic acid/anhydride or mixtures thereof with organic solvents can be employed as vaporized feeds with hydrogen in a similar process but substituting instead a reduced copper-zinc catalyst. In practice, it is possible to obtain high yields of gamma-butyrolactone, but the catalysts often become deactivated through tar and coke formation within a relatively short time.

It has now been discovered that yields of gamma-butyrolactone in excess of 90% can be achieved by mixing vapors of water with the feed of maleic acid/anhydride or succinic acid/anhydride, or mixtures of any of the foregoing, and passing this aqueous vapor and hydrogen, preferably in excess, over a metallic catalyst capable of hydrogenolyzing a carboxylic group to a methyleneoxy group. It is an unique advantage of this process to make use of an aqueous solution of crude maleic acid, such as is produced by making maleic anhydride by oxidation of benzene or mixed $C_4$ hydrocarbons over a vanadium catalyst. However, apart from this obvious economic advantage, it is a most unexpected advantage in the present invention to discover that the water in the feed stock apparently plays a very important role in keeping the heterogeneous system clean. There appears to be a supression in the coke and tar formation normally found when non-aqueous feed stocks, and especially when feed stocks in vaporized organic solvents, are employed. As a result, the process according to this invention can be run for a much longer time than those in the prior art, thus delaying the time when it becomes necessary to shut the reactor for replenishment or regeneration of the catalyst.

It is very unexpected to find that water vapor in the feed provides the advantages observed because: (i) water is a byproduct of the hydrogenolysis and/or cyclization reaction(s) and its presence in the feed stock would be expected to have an adverse, depressing effect on the yield of desired gamma-butyrolactone; and (ii) metallic catalysts for hydrogenolyzing carboxylic functions (e.g., the reduction of glycerides to alcohols) are known to be very sensitive to the presence of moisture, requiring that the reaction environment be kept totally dry or at most have a water content of no greater than 1% by weight. In the present process, water contents of up to and greater than 70% by weight can be tolerated without any destruction of catalyst effectiveness.

DESCRIPTION OF THE INVENTION

According to the present invention, there is provided a process for the production of gamma-butyrolactone which comprises vaporizing maleic acid, maleic anhydride, succinic acid, succinic anhydride or a mixture thereof, and water, and contacting the resulting vapors and hydrogen with a metallic catalyst capable of hydrogenolyzing a carboxylic group to a methyleneoxy group.

With respect to the metallic catalyst, metals and combinations which are capable of hydrogenolyzing a carboxylic group, e.g., an ester group, a carboxyl group, a dicarboxylic anhydride group, and the like, to a group containing at least one methyleneoxy function are well known to those skilled in the art. Merely by way of illustration, such catalysts can comprise solids consisting of metals and metal oxides, and will include nickel, cobalt, molybdenum, tungsten, copper, zinc and chromium, oxides and sulfides thereof, and metallic platinum and paladium and oxides thereof. More specifically, they will include copper with oxides of zinc, nickel, chromium or manganese, and illustratively, they will be reduced copper-ammonium chromate, copper-chromium oxide (also frequently referred to as copper-chromite), copper-zinc, nickel, zinc oxide, chromic oxide, $Ni-SiO_2$, PdO, W, Ni-sulfide, $CoMo-Al_2O_3$, $PtO_2$, and the like. The preferred catalysts will include oxides of copper, zinc, chromium, manganese, nickel or a mixture of any of the foregoing. Especially preferred catalyst will be reduced copper-chromite catalysts or copper-zinc catalyst. The reduced copper-chromite catalyst can be made by reacting copper nitrate and chromium oxide in the presence of ammonia, filtering with vacuum, washing with water and roasting. (See, e.g., Adkins, U.S. Pat. No. 2,091,800.) The copper-zinc catalyst can be prepared by reacting sodium carbonate with cupric nitrate and zinc nitrate, washing the precipitate with water, optionally mixing with asbestos, and drying to form granules. (See, e.g., U.K. Pat. No. 1,168,200.) The catalysts may be used in the form of pellets, pellet particles or may be deposited on or mixed with a carrier as is well known. The catalysts are also available from a number of commercial sources. For example, a suitable pre-reduced copper-chromite catalyst is available from the Girdler Company, under product designation G-13, in the form of ⅛ inch pellets; and copper-zinc catalysts are avialable from the Girdler Company under the product designation G-66 ARS and G-66-BRS (these must be reduced with hydrogen before use).

In carrying out the production of gamma-butyrolactone, any one or a mixture of maleic acid, maleic anhydride, succinic acid or succinic anhydride may be vaporized with water and passed with hydrogen through a catalyst bed which has been heated, e.g., to from 100° to 400° C., preferably to from 150° C. to about 325° C. In order to obtain the maximum yield of gamma-butyrolactone, preferably at least about 10 moles of hydrogen are used for each mole of acid or anhydride in the feed. Preferably, even a larger excess of hydrogen is used, e.g., up to about 100:1 or so, but there is no advantage in using more.

The ratio of acid/anhydride to water in the feed stock can vary widely. For example, the weight ratio will be in the range of from 1.0 to 99.0 parts of acid/anhydride to 99.0 to 1.0 parts of water. Preferably, the ratio will be from 10 to 60 parts of acid/anhydride to 90 to 40 parts of water and, especially preferably, from about 30 to 40 parts of acid/anhydride to 70 to 60 parts of water. The latter, preferred ratios are conveniently obtained by vaporizing an appropriate aqueous solution. On the other hand, the acid/anhydride and the water can be separately vaporized, then mixed before being brought into contact with the catalyst.

The reaction can be carried out an sub-atmospheric, atmospheric and super-atmospheric pressure, but it is convenient to operate at atmospheric pressure or at a pressure of from 1 atmosphere up to about 15 atmospheres.

If the reaction is carried out by passing the vaporized mixture through a reactor containing the catalyst, the vapors issuing from the reactor are condensed and the product separated by conventional methods such as crystallization, distillation, etc.

DESCRIPTION OF THE PREFERRED EMBODIMENTS

The following examples illustrate the process of the present invention. They are not to be construed to limit the invention. Unless otherwise indicated, all parts are by weight.

The reaction system consists of a tubular reactor of the type described in each example. The catalyst charge is as described in each example. The reactor tube is heated by immersion in a hot oil bath. A thermowell in the reactor permits measurement of catalyst bed temperature. In the system, before the reactor, there is a tubular vaporizer for the feedstock. The vaporizer is heated with an external oil bath maintained at 270°–275° C. Before the vaporizer is a reservoir to hold the feedstock, if liquid. The rate of hydrogen flow is measured at the exit port on the reactor, and the rate of flow of the feedstock is measured volumetrically on the liquid in the reservoir. The vapors exiting from the reactor are fed to a water cooled condenser-receiver and the liquified products are collected and analyzed for gamma-butyrolactone, unreacted starting materials and by-products, by gas phase chromatography.

EXAMPLE 1

A feedstock comprising 30 wt.% of maleic acid/70 wt.% water is placed in the reservoir. A reduced copper-chromite catalyst, 114 g. of ⅛ inch pellets (Girdler G-13), is placed in a 8 inch × 1 inch (OD) glass tube reactor which is heated at 285°–290° C. The feedstock is introduced into the vaporizer at a liquid flow rate of 4 ml./hr. and the vaporized mixture is mixed with hydrogen and fed to the reactor. The rate of hydrogen flow measured at the exit port is 500 cm³/minute. The gases passing from the reactor are cooled and liquid condensate is collected. The yield of gamma-butyrolactone in the liquid phase is 90% of theoretical and the amount of succinic acid anhydride corresponds to 5% of theory, and the remainder, 5%, is propionic acid, butyric acid, propanol and n-butanol.

For comparison purposes the process is repeated, feeding vapors of maleic anhydride and hydrogen, but no water, to the reactor.

Although the process with water vapor in the feed can be run for more than 750 hours without building up tar and coke in the reactor, without water a substantial amount of coke and tar formation is evident in much less time. Thus the present process proceeds without substantial deactivation of the catalyst.

EXAMPLE 2

The procedure of Example 1 is repeated with the following variations in conditions and results:
 Reactor: 110 inch × 1 inch (OD) copper tube
 Catalyst: 1760 g. of 3/16 inch × ⅛ inch pellets of copper chromite (Girdler G-13)
 Feed: 30 wt.% maleic acid/70 wt.% water
 Feed rate: 30 ml./hr.
 H$_2$ flow: 600 cc./min. at the exit port
 Catalyst bed temp: 285°–290° C.
 Yield:
  85–90% gamma-butyrolactone
  5–10% succinic anhydride
  5% propionic acid, butyric acid, propanol, n-butanol
 Running time: 750 hours

COMPARATIVE EXAMPLE 2A

The procedure of Example 1 is repeated with the following variations in conditions and results:
 Reactor: 8 inch × 1 inch (OD) glass tube
 Catalyst: 106 g. of 3/16 inch × ⅛ pellets of copper chromite (Girdler G-13)
 Feed: 50–50wt.% maleic anhydride/gamma-butyrolactone
 Feed rate: 10 ml./hr.
 H$_2$ flow: 500 cc./min. at exit port
 Catalyst bed temperature: 280° C.
 Yield:
  90% gamma-butyrolactone
  3% succinic acid/anhydride
  5–7% propionic acid, butyric acid, propanol and n-butanol
 Running time: 100 hours During the running there was observed a significant build-up of tar on the catalyst surface and in the vaporizer.

EXAMPLE 3

The procedure of Example 2 is repeated, except that the catalyst bed temperature is increased to 315° C.
 Yield:
  90–95% gamma-butyrolactone
  5% succinic acid/anhydride
  <3% propionic acid, butyric acid, propanol and n-butanol
 Running time: 24 hours There is no observable build-up of tar.

EXAMPLE 4

The procedure of Example 1 is repeated, except that the feed rate is increased from 4 ml./hr. to 11 ml./hr.
 Yield:
  70% gamma-butyrolactone
  25% succinic acid/anhydride
  5% propionic acid, butyric acid, propanol and n-butanol
 Running time: 6 hours There is no observable build-up of tar.

EXAMPLE 5

The procedure of Example 1 is repeated, except that the feed consists of 7 wt.% succinic acid/93 wt.% water.
Yield:
>95% gamma-butyrolactone
<5% propionic acid, butyric acid, propanol and n-butanol
Running time: 3 hours
There is no observable build-up of tar.

EXAMPLE 6

The procedure of Example 1 is repeated with the following conditions and results:
Reactor: 8 inch × 1 inch (OD) glass tube
Catalyst: 82 g. of 3/16 inch × ⅛ inch pellets of copper-zinc-alumina (Girdler, G-66 ARS, pre-reduced with hydrogen before use)
Feed: 30 wt.% maleic acid/70 wt.% water
Feed rate: 4 ml./hr.
$H_2$ flow: 500 cc./min. at exit port
Catalyst bed temp.: 290° C.
Yield:
90% gamma-butyrolactone
5-10% succinic acid/anhydride
<2% propionic acid, butyric acid, propanol and n-butanol
Running time: 30 hours
There is no observable build-up of tar.

EXAMPLE 7

The procedure of Example 1 is repeated with the following conditions and results:
Reactor: 24 inch × 2 inch (OD) stainless steel tube
Catalyst: 625 g. of 3/16 inch ⅛ inch pellets of copper-zinc (Girdler, G-66-BRS, pre-reduced with hydrogen before use)
Feed: 30 wt.% maleic acid/70 wt.% water
Feed rate: 30 ml./hr.
$H_2$ flow: 500 cc./min. at exit port
Catalyst temp.: 280° C.
Yield:
85-90% gamma-butyrolactone
5-10% succinic acid/anhydride
5% propionic acid, butyric acid, propanol and n-butanol
Running time: 6 hours
There is no observable build-up of tar.

EXAMPLE 8

The procedure of Example 1 is is repeated with the following conditions and results:
Reactor: 8 inch × 1 inch (OD) glass tube
Catalyst: 106 g. of 3/16 inch × ⅛ inch pellets of copper-zinc-chrome (Girdler, T-359)
Feed: 30 wt.% maleic acid/70 wt.% water
Feed rate: 4 ml./hr.
$H_2$ flow: 500 cc./min. at exit port
Catalyst bed temp.: 270° C.
Yield:
90% gamma-butyrolactone
5-10% succinic acid/anhydride
<2% propionic acid, butyric acid, propanol and n-butanol
Running time: 1 hour
There is no observable build-up of tar.

EXAMPLE 9

The procedure of Example 1 is repeated with the following conditions and results:
Reactor: 110 inch × 1 inch (OD) copper tube
Feed: 30 wt.% maleic acid/70 wt.% water
Feed rate: 30 ml./hr.
$H_2$ flow: 1500 cc./min. at exit port; 2 atm. $H_2$ gauge pressure
Catalyst bed temp.: 290°-300° C.
Yield:
>90% gamma-butyrolactone
<5% propionic acid, butyric acid, propanol and n-butanol
Running time: 100 hours
There is no observable build-up of tar.

EXAMPLE 10

The procedure of Example 9 is repeated, except that the feed rate is increased to 60 ml./hr.
Yield:
90-95% gamma-butyrolactone
3-5% succinic anhydride
<1% propionic acid, butyric acid, propanol, n-butanol
Running time: 24 hours
There is no observable build-up of tar.

EXAMPLE 11

The procedure of Example 9 is repeated except that the feed rate is increased to 100 ml./hr., $H_2$ flow is increased to 2000 cc./min. at the exit port, and 3 atm. $H_2$ gauge pressure is used.
Yield:
90-95% gamma-butyrolactone
3-5% succinic anhydride
<1% propionic acid, butyric acid, propanol and n-butanol
Running time: 6 hours
There is no observable build-up of tar.

Typical chemical and physical properties of the catalysts used in the above-mentioned examples are as follows:

| Examples | 1-5&9-11 | 6 | 7 | 8 |
| --- | --- | --- | --- | --- |
| Chemical Composition: | 45% Cu | 45.8% Zn | 57.5% Zn | 5.7% Cu |
|  | 55% Cr | 23.5% Cu | 27.5% Cu | 52.7% Zn |
|  |  | 10.0% Al |  | 13% Cr |
| Bulk density, lbs./cu.ft.: | 75 | 75 | 80 | 90 |
| Crush strength, lbs.: | — | 8 | 8 | — |

While the foregoing discloses certain specific embodiments of the invention, it is understood that there are many modifications which obviously fall within the intended scope of the invention. Accordingly, the invention is defined by the appended claims.

I claim:
1. In a vapor phase process for the production of gamma-butyrolactone by passing a vaporized feed of maleic acid, maleic anhydride, succinic acid or succinic anhydride or a mixture thereof with hydrogen over a metallic catalyst capable of hydrogenolyzing a carboxylic group to a methyleneoxy group, the improvement which comprises the steps of:
  i. providing a vaporized mixture of (a) maleic acid, maleic anhydride, succinic acid, succinic anhydride or a mixture thereof, and (b) water at a ratio of from 10 to 60 parts by weight of acid/anhydride to 90 to 40 parts by weight of water, and
  ii. contacting the resulting vaporized mixture and hydrogen in the vapor phase with a metallic catalyst capable of hydrogenolyzing a carboxylic group to a methyleneoxy group.

2. A process as defined in claim 1 wherein said metal catalyst includes copper oxide, zinc oxide, chromium oxide, manganese oxide, nickel oxide or a mixture of any of the foregoing.

3. A process as defined in claim 1 wherein said catalyst has been pre-reduced with hydrogen before being contacted with said vaporized mixture and hydrogen.

4. A process as defined in claim 2 wherein said catalyst is a copper-chromite catalyst or a copper-zinc catalyst.

5. A process as defined in claim 1 wherein said vaporized mixture consists essentially of maleic acid and water.

6. A process as defined in claim 5 wherein the maleic acid consists essentially of from about 10 to about 60 percent by weight of said vaporized mixture.

7. A process as defined in claim 6 wherein said maleic acid consists essentially of from about 30 to about 40 percent by weight of said vaporized mixture.

8. A process as defined in claim 1 wherein the molar ratio of hydrogen to said maleic acid, maleic anhydride, succinic acid, succinic anhydride or mixture thereof is in excess of about 10:1.

9. A process as defined in claim 1 wherein the catalyst is in a fixed bed and is maintained at a temperature of from about 100° C. and 400° C.

10. A process as defined in claim 9 wherein the catalyst temperature is maintained at from about 150° C. to about 325° C.

11. A process as defined in claim 1 wherein the pressure is from 1 to 15 atmospheres.

12. In a vapor phase process for producing gamma-butyrolactone by passing a vaporized feed of maleic acid with hydrogen over a metallic catalyst capable of hydrogenolyzing a carboxylic group to a methyleneoxy group, the improvement which comprises the steps of:
  i. providing a vaporized mixture of (a) from about 10 to about 50 weight percent of maleic acid in (b) water, said mixture having a ratio of from 10 to 50 parts by weight of acid to 90 to 50 parts by weight of water,
  ii. contacting the resulting vaporized mixture and hydrogen in the vapor phase at a pressure of from 1 to 5 atmospheres and at a temperature between about 150° C. and 325° C. in the presence of a reduced copper-chromite or a reduced copper-zinc catalyst,
  iii. condensing the resulting product vapors, and
  iv. recovering said gamma-butyrolactone therefrom.

13. A process as defined in claim 12 wherein the molar ratio of hydrogen to maleic acid is in excess of about 10:1.

14. A process as defined in claim 12 wherein said catalyst is a reduced copper-chromite catalyst having a weight ratio of between about 10:1 to 1:1 of $CuO:Cr_2O_3$ prior to reduction.

15. In a vapor phase process for the production of gamma-butyrolactone by passing a vaporized feed of maleic acid, maleic anhydride, succinic acid or succinic anhydride or a mixture thereof with hydrogen over a metallic catalyst capable of hydrogenolyzing a carboxylic group, the improvement which comprises the steps of:
  i. providing a vaporized mixture of (a) maleic acid, maleic anhydride, succinic acid, succinic anhydride or a mixture thereof, and (b) water at a ratio of from 10 to 60 parts by weight of acid/anhydride to 90 to 40 parts by weight of water, and
  ii. contacting the resulting vaporized mixture and hydrogen in the vapor phase with a metallic catalyst capable of hydrogenolyzing a carboxylic group to a methyleneoxy group and which includes copper oxide, zinc oxide, chromium oxide, manganese oxide, nickel oxide or a mixture thereof, and wherein the molar ratio of hydrogen to said maleic acid, maleic anhydride, succinic acid, succinic anhydride or mixture thereof is in excess of about 10:1, the catalyst is in a fixed bed and is maintained at a temperature of from about 100° C. to 400° C., and the pressure is from 1 to 15 atmospheres.

16. A process as defined in claim 15 wherein said metallic catalyst is a copper-chromite catalyst or a copper-zinc catalyst which has been pre-reduced with hydrogen before being contacted with said vapors and hydrogen.

* * * * *